US00PP19181P3

(12) United States Plant Patent
Moon

(10) Patent No.: US PP19,181 P3
(45) Date of Patent: Sep. 2, 2008

(54) TRIDENT MAPLE TREE NAMED 'ABFSS'

(50) Latin Name: *Acer buergerianum*
Varietal Denomination: ABFSS

(75) Inventor: Dwayne C. Moon, Loganville, GA (US)

(73) Assignee: Southern Selections, LLC, Loganville, GA (US)

( * ) Notice: Subject to any disclaimer, the term of this patent is extended or adjusted under 35 U.S.C. 154(b) by 197 days.

(21) Appl. No.: 11/302,934

(22) Filed: Dec. 14, 2005

(65) Prior Publication Data

US 2007/0136906 P1 Jun. 14, 2007

(51) Int. Cl.
*A01H 5/00* (2006.01)

(52) U.S. Cl. ..... Plt./224

(58) Field of Classification Search ..... Plt./224
See application file for complete search history.

(56) References Cited

U.S. PATENT DOCUMENTS

PP9,576 P 6/1996 Glenn
2007/0136906 P1 * 6/2007 Moon ..... Plt./224

OTHER PUBLICATIONS

U.S. Appl. Ser. No. 10/900653 filed Feb. 2, 2006 by Moon.

* cited by examiner

*Primary Examiner*—Kent L. Bell
*Assistant Examiner*—Georgia Helmer
(74) *Attorney, Agent, or Firm*—Polster, Lieder, Woodruff & Lucchesi, L.C.

(57) ABSTRACT

A Trident maple (*Acer buergerianum*) named 'ABFSS,' which has an upright fastigiate canopy and is capable of being reproduced reliably from vegetative cuttings.

7 Drawing Sheets

Latin name of genus and species: *Acer buergerianum.*

Variety denomination: Trident maple named 'ABFSS'.

BACKGROUND OF THE INVENTION

Discovery

I discovered my new tree from a group of seedlings purchased from a nursery in Texas. The group of seedlings were growing in a nursery production field of Trident maples as randomly open pollinated *Acer buergerianum* seedlings during the fall of 1997. This group of seedlings was grown in a liner field and then transplanted to an adjacent production field in Loganville, Walton County, Ga. during the winter of 1999. It was here that I discovered the claimed cultivar 'ABFSS.'

Propagation

'ABFSS' was asexually propagated by the method of vegetative cutting at my direction in the summer of 2002 in Loganville, Ga. Softwood cuttings three to five inches long were treated with 3000 ppm potassium indole-3-butyric acid (KIBA). The cuttings were then placed in peat pots filled with horticultural growing media and then intermittently misted for a period of five to six weeks. Currently our success rate for this method exceeds 70%.

Uniqueness

Seedling Trident maples are very diverse due to genetic variability in leaf size, branch structure, bark exfoliation and growth rate. The claimed cultivar was notably different from others in this seedling block due to its vertical branch structure and fastigiate form. This invention has not been observed under all possible environmental conditions, but the progeny of 'ABFSS' have repeatedly shown that these characteristics are genetically stable.

Use

'ABFSS' has been observed for several years, and I believe it to be very useful for urban street plantings and commercial sites where a narrow, upright, medium-sized maple species is required.

SUMMARY OF THE INVENTION

Background

*Acer buergerianum* is an oval-rounded to rounded small maple native to China. It performs well in the more acidic soils of zones 5 to 8 in the United States. It has been successfully grown from the mid-Atlantic area south to northern Florida and west to the eastern part of Texas and Oklahoma. I expect my new variety of Trident maple to perform as well as the species in these regions.

Industry Representation

Trident maple is typically seedling grown through random open-pollination. This method creates great variability of canopy height and width, branch structure, leaf color and size, and bark exfoliation. This genetic diversity has limited the landscape use of this tree due to a lack of uniformity. Presently, the only commercially available cultivars of this species of which I am aware are *Acer buergerianum* 'ABTIR' Streetwise, U.S. Plant Pat. No. 9,576 and *Acer buergerianum* 'ABMTF' U.S. Plant patent application Ser. No. 10/900,658.

My new variety differs from 'ABTIR' in the following characteristics: (1) tight, vertical branch angles and (2) fastigiate form. According to the description of 'ABTIR,' this tree reached a height of eighteen feet and a spread of twelve feet wide after eight years while 'ABMTF' grew to a height of twenty-one feet and spread of thirteen feet after a period of five years. My claimed cultivar 'ABFSS' had a height of eighteen feet and spread of six feet when it was transplanted in December of 2004 (a period of five growing seasons).

DESCRIPTION OF THE PHOTOGRAPHS

The accompanying photographs illustrate this new Trident maple variety with color as true as reasonably possible in this type of color photography.

DETAILED DESCRIPTION

Botanical Description of the Plant

Figure 1:
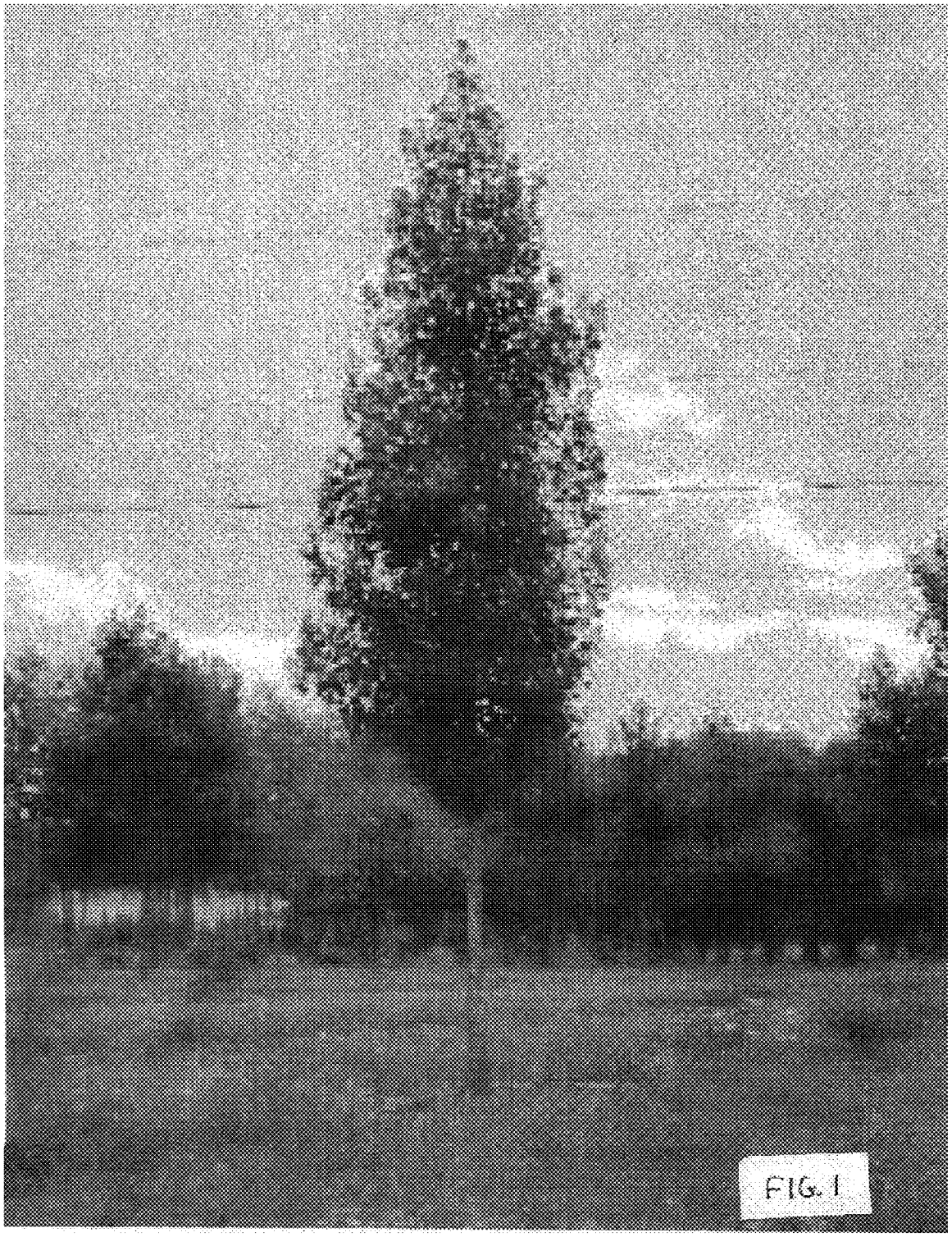
FIG. 1 is a photograph of the claimed cultivar taken in the summer of 2003 at an observation area showing form and habit. The age of the plant shown in FIG. 1 is 5 years old.
Figure 2:
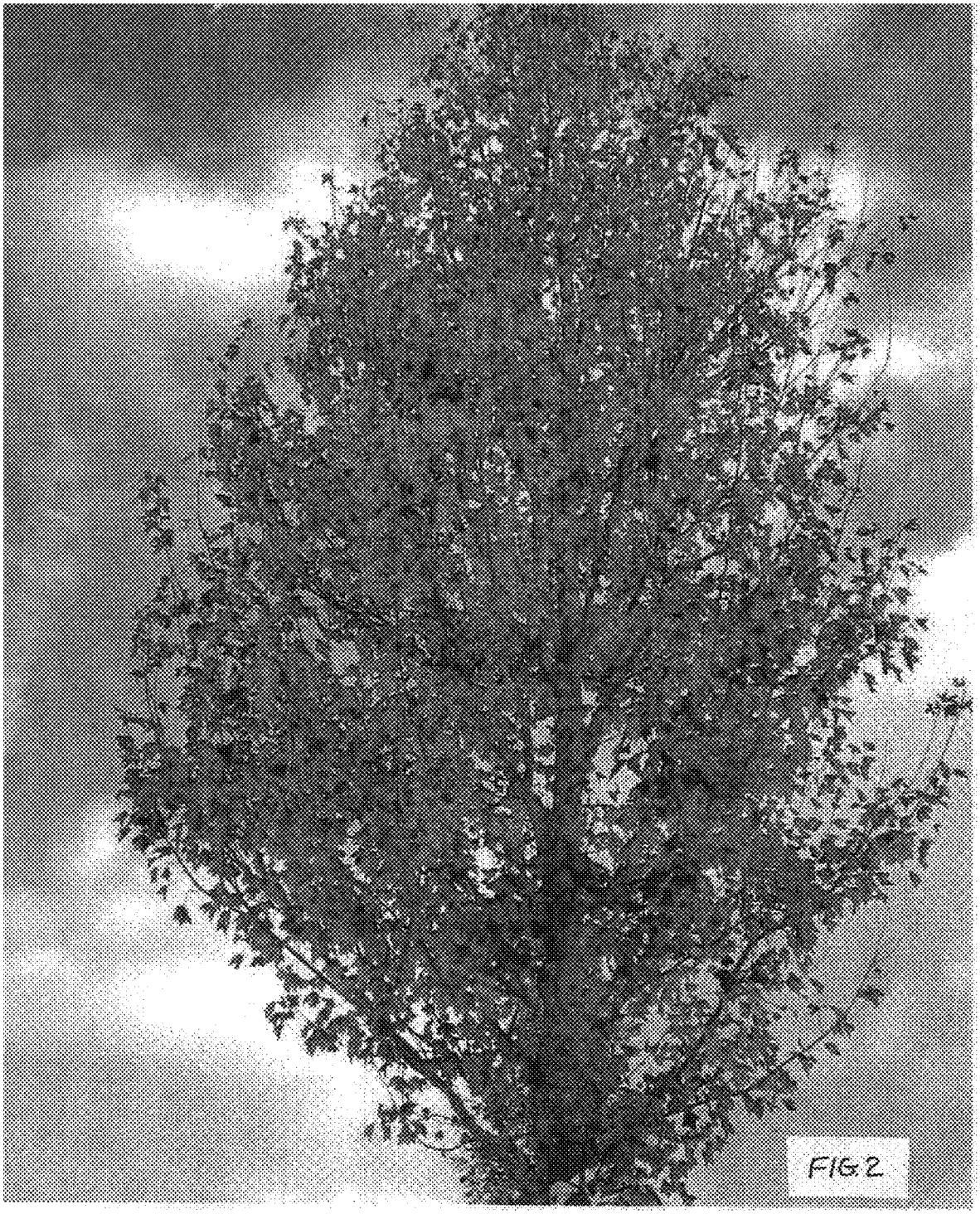
FIG. 2 is a photograph of the claimed cultivar in the fall of 2004 showing variations in fall color and branch structure. The age of the plant shown in FIG. 2 is 6 years old.
Figure 3:
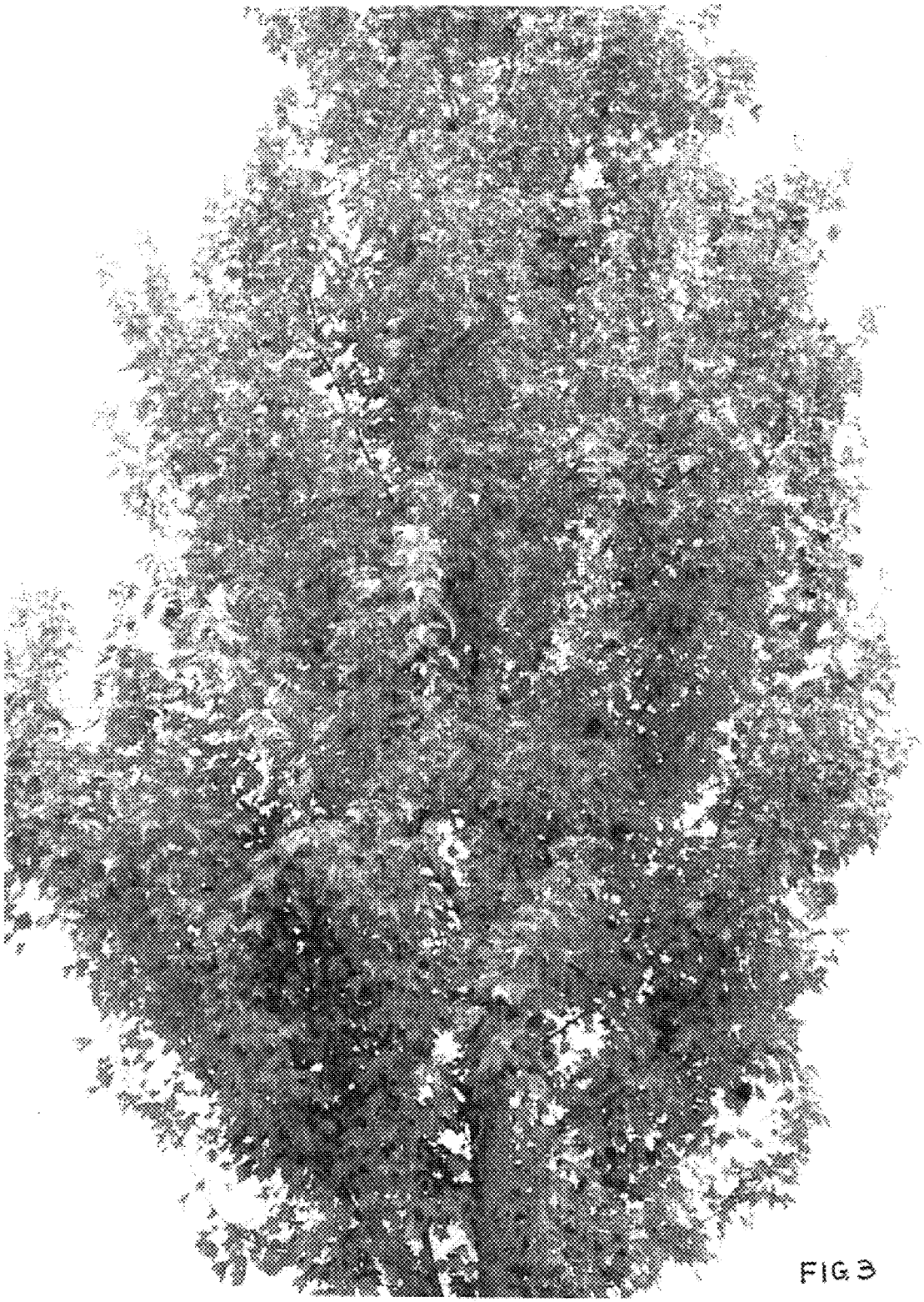
FIG. 3 is a photograph of the interior canopy of the claimed cultivar. The age of the plant shown in FIG. 3 is 6 years old.
Figure 4:
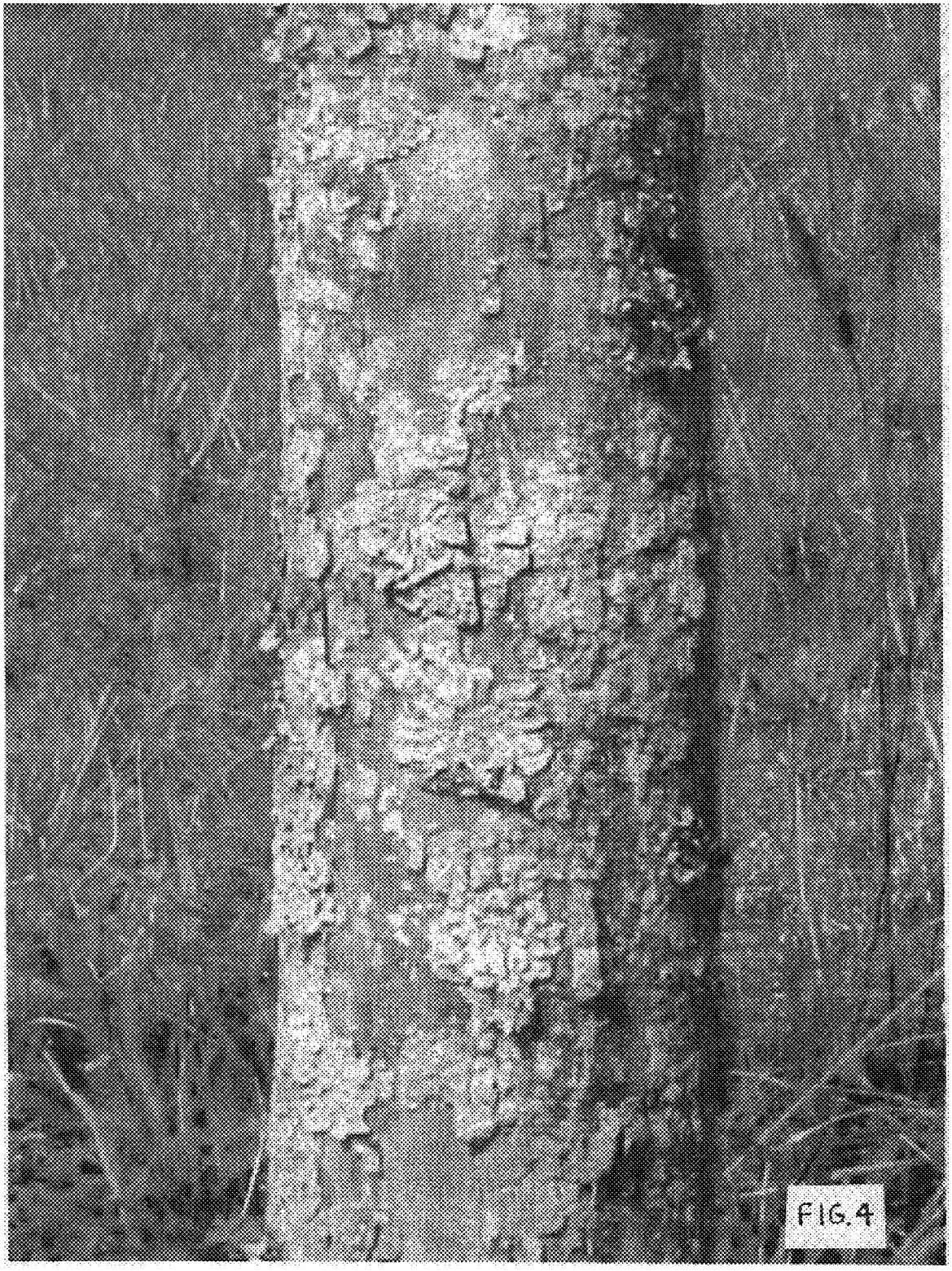
FIG. 4 is a photo of the bark of the claimed cultivar at 4" caliper showing color, texture and minimal exfoliation. The age of the plant shown in FIG. 4 is 8 years old.
Figure 5:
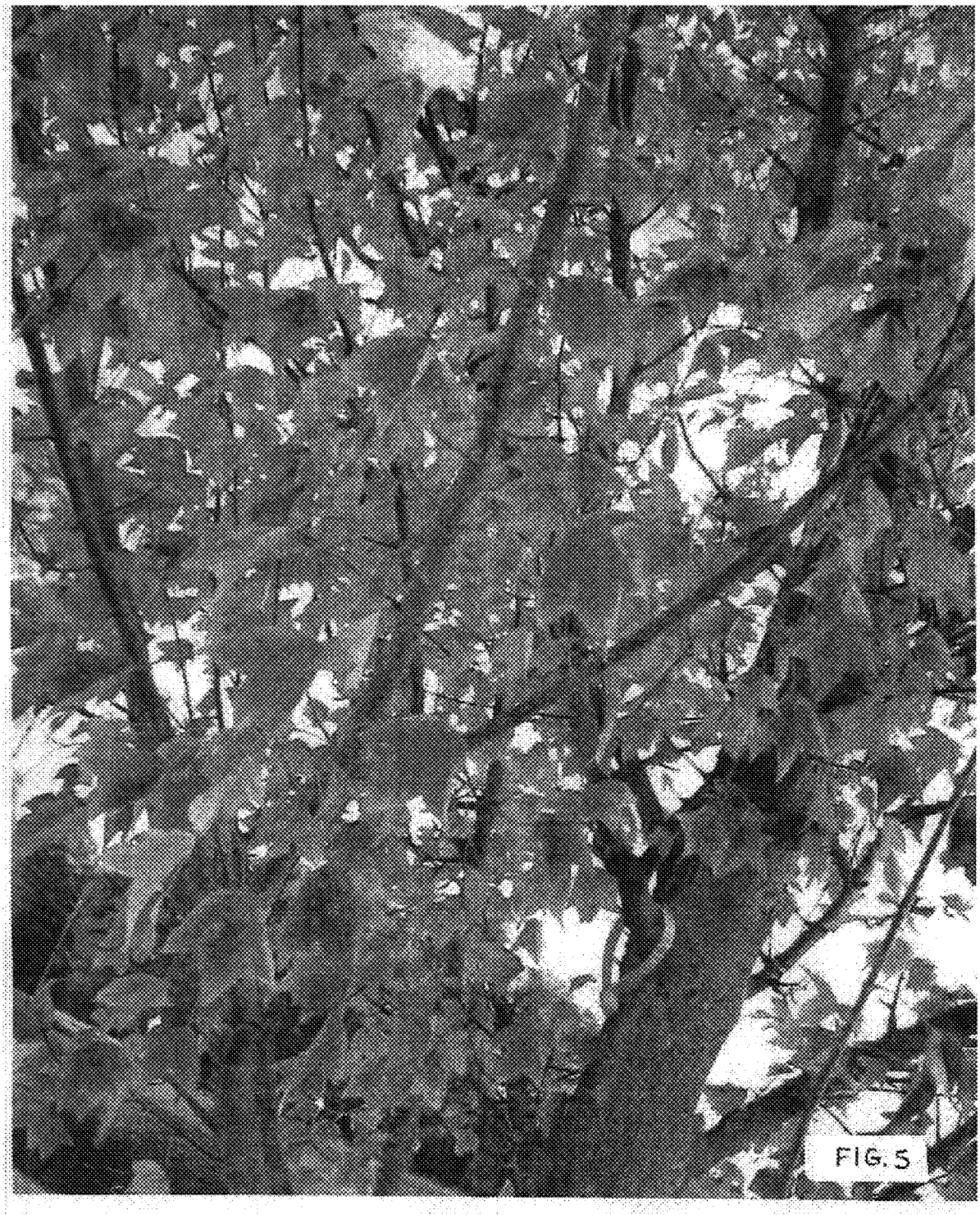
FIG. 5 is a photo close-up of fall foliage and variation of color. The age of the plant shown in FIG. 5 is 8 years old.
Figure 6:
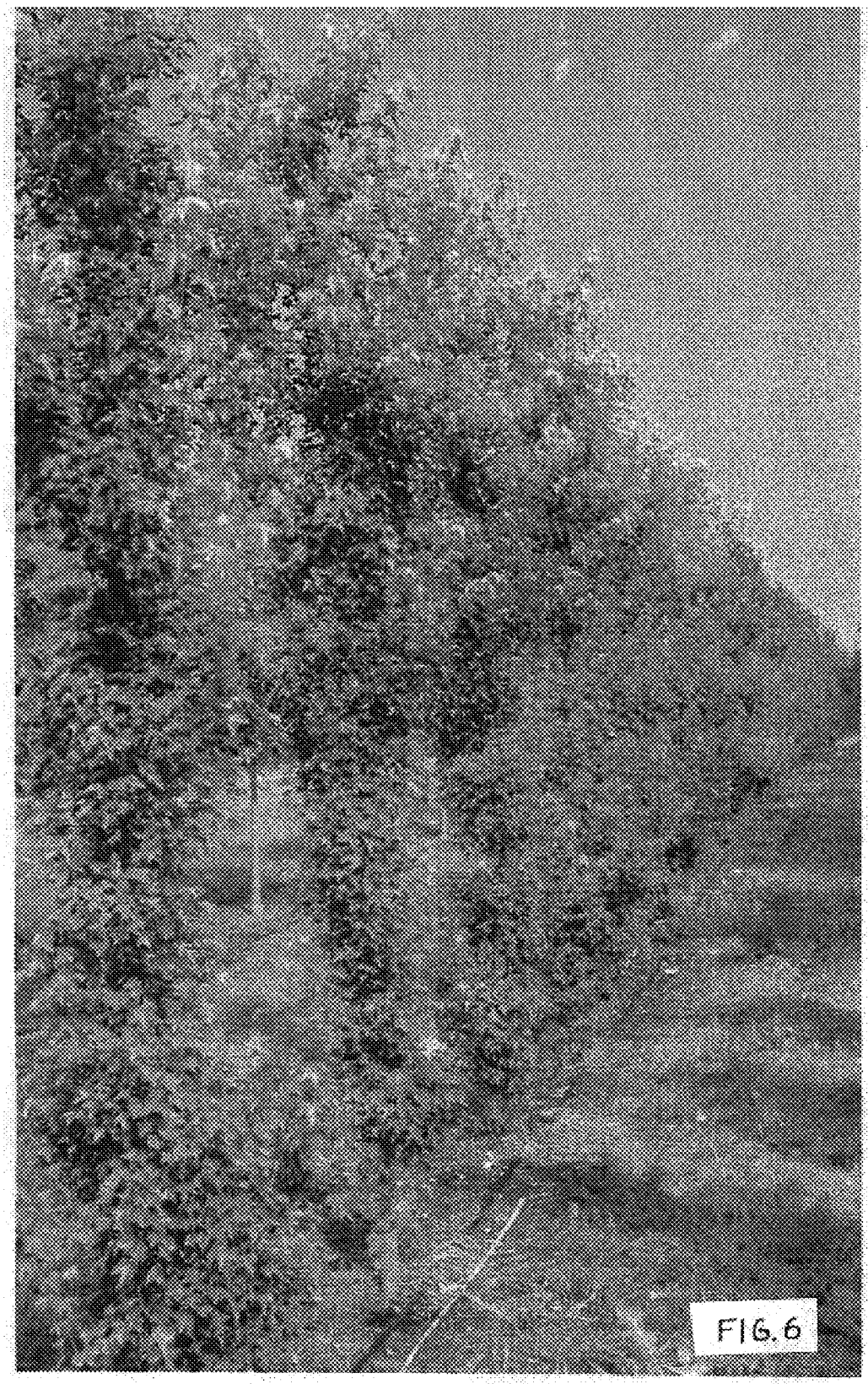
FIG. 6 is a field row shot of progeny at two inch caliper. The age of the plant shown in FIG. 6 is 4 years old.
Figure 7:
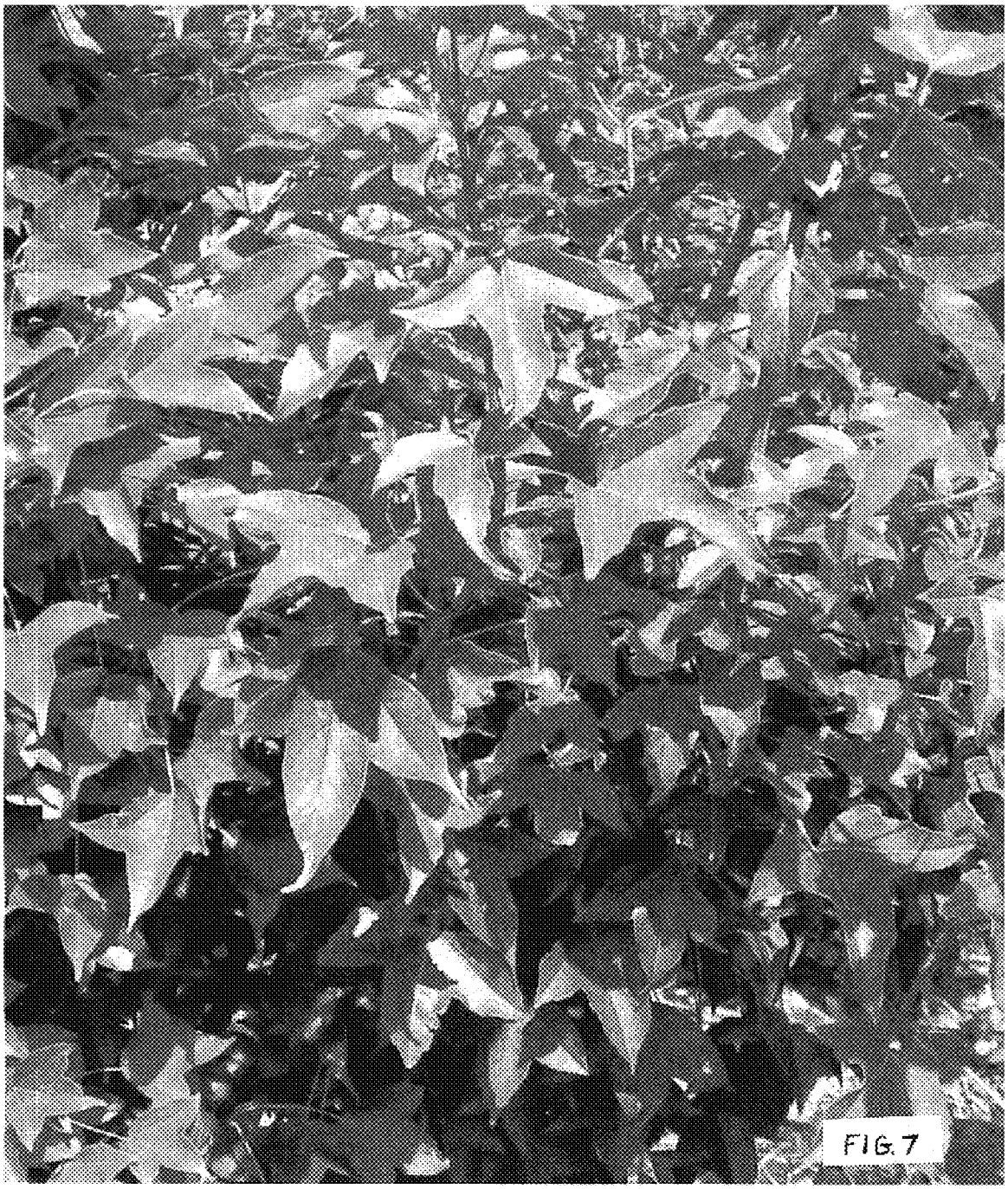
FIG. 7 is a photo of summer foliage showing leaf shape. The age of the plant shown in FIG. 7 is 4 years old.

This invention has not been observed under all possible environmental conditions. The phenotype may vary with variations in growing environment, without, however, any variations in genotype. 'ABFSS' is currently being grown in fields adjacent to 6327 Hwy. 20, Loganville, Walton County, Ga. This particular area of Walton County has a clay loam soil type located in USDA Zone 7 and has an average rainfall of 30–60 inches annually. The following is a detailed description of 'ABFSS' Trident maple with color terminology in accordance with The Royal Horticulture Society (R.H.S.) colour chart, except where the context indicates a term having its ordinary dictionary meaning.

Parentage: Chance seedling of random open-pollinated Trident maple parentage purchased from supplier in Texas.

Propagation: Genetically stable characteristics reproduced through asexual, vegetative softwood cuttings.

Locality where grown and observed: City of Loganville, County of Walton, State of Georgia.

Size and growth rate: At time of transplant, the claimed cultivar was five years old and measured 4" caliper at 6 inches the ground. The height was 18 feet and the width was 6 feet, thus providing a height to width ratio of 3 to 1. Prior to transplanting, the tree had an average growth rate of 1" caliper per year. This same rate of growth has been evident in the progeny.

Tree shape: Upright fastigiate with very dense foliage.

Trunk: Smooth and unfluted with minimal exfoliation. Some stripe detail is evident which causes the coloring to vary between greyed-green (RHS 197A) and greyed-brown (RHS 199D).

Branching habit: More dense than species, primary lower branching emerges at about 30–35 degree angle with 20% of branch end curving upward. Branching toward the top third of the tree has 20–25 degree angles.

Branches: Hardwood branching has a greyed-green (RHS 197C) to (RHS 198B) coloring while soft wood branching is yellow-green (146C). Wood is rigid but smooth, with small grayed white lenticels.

Foliage: Mature leaves are semi-gloss tri-lobed with each lobe being triangular. Width between outer lobes averages two to three inches. Distance from base of leaf to middle lobe is also two to three inches. Margin of leaf in lobe section tends to be slightly serrate. The color of the leaf front is a medium green (RHS 143A) while the back side is a greyed-green (RHS 138B). As new growth emerges, the coloring is a greyed-red (RHS 176C). During the fall, foliage is yellow-orange (RHS 33B). The petiole is a yellow-green (RHS 146C), measures about two inches and is smooth.

Buds: Conical, reddish-brown (RHS 176C), ¼ inch long and pyramidal.

Stems: Slender, grayed-brown (RHS 199D) with pubescence.

Flower: Small, greenish-yellow (RHS 145B) in slightly rounded clusters during mid-spring.

Fruit: Yellowed-green (RHS 144C) double samaras ¾ inch to one inch long and ¼ inch wide, formed in autumn.

Disease and pest: During the evaluation period, I have not seen disease or pest damage on the parent or the progeny.

Hardiness: USDA Plant Hardiness Zone 5–8.

I claim:

1. A new and distinct variety of Trident maple tree (*Acer buergerianum*) named 'ABFSS' substantially as illustrated and described herein.

* * * * *